United States Patent [19]

Yeh et al.

[11] Patent Number: 5,183,914
[45] Date of Patent: Feb. 2, 1993

[54] ALKOXYSILANES AND OLIGOMERIC ALKOXYSILOXANES BY A SILICATE-ACID ROUTE

[75] Inventors: Li-Tain Yeh, Cleveland; Malcolm E. Kenney, Cleveland Heights, both of Ohio; Gary N. Bokerman; John P. Cannady, both of Madison, Ind.; Ollie W. Marko, Carrollton, Ky.

[73] Assignees: Dow Corning Corporation, Midland, Mich.; Case Western Reserve University, Cleveland, Ohio

[21] Appl. No.: 692,413

[22] Filed: Apr. 29, 1991

[51] Int. Cl.$^5$ .................................................. C07F 7/18
[52] U.S. Cl. ..................... 556/467; 556/457; 556/458; 556/470
[58] Field of Search ................. 556/470, 467, 457, 458

[56] References Cited

U.S. PATENT DOCUMENTS 2,727,054 12/1955 Wright ................................. 556/470
4,923,687 5/1990 Schork et al. ....................... 556/470

OTHER PUBLICATIONS

Goodwin et al., Inorganic and Organometallic Polymers, ACS symposium 360 (1987).
Goodwin et al., Advances in Chemistry, 224 (1990).
Goodwin et al., Polym. Prepr. Am. Chem Soc Div. Polym Chem, 27, 107 (1986).
Goodwin et al., Inorg Chem, 29, 1216 (1990).

Primary Examiner—Paul F. Shaver
Attorney, Agent, or Firm—Roger E. Gobrogge

[57] ABSTRACT

The present invention relates to a novel method of preparing alkoxysilanes and oligomeric alkoxysiloxanes. The method comprises reacting a metal silicate with an acid selected from the group consisting of sulfurous acid and acids with a pKa greater than about 2.5 in the presence of an alcohol. The resultant product is then reacted with an alcohol to form the alkoxysilane or oligomeric alkoxysiloxane, depending on the starting silicate. This method is particularly valuable since the reaction conditions are mild and the reactants are readily available.

30 Claims, No Drawings

ALKOXYSILANES AND OLIGOMERIC ALKOXYSILOXANES BY A SILICATE-ACID ROUTE

BACKGROUND OF THE INVENTION

The present invention relates to a novel method of preparing alkoxysilanes and oligomeric alkoxysiloxanes. The method comprises reacting a metal silicate with an acid selected from the group consisting of sulfurous acid and acids with a pKa greater than about 2.5 in the presence of an alcohol. The resultant product is then reacted with an alcohol to form the alkoxysilane or oligomeric alkoxysiloxane, depending on the starting silicate. This method is particularly valuable since the reaction conditions are mild and the reactants are readily available.

Several methods of producing alkoxysilanes are known in the art. The most well known and often used of these methods involves the reaction of silicon tetrachloride with an alcohol. Despite the high yields which can be obtained, this method is disadvantageous in that it is a 2-step process initially requiring the formation of silicon tetrachloride.

In order to avoid this roundabout approach, a method has been developed that yields alkoxysilanes by a 1-step reaction using elemental silicon and alcohols. Unfortunately, elemental silicon is generally produced from silica by a very endothermic and thus costly reaction.

Several routes to oligomeric alkoxysiloxanes have also been developed. For instance, in one route silicon tetrachloride is treated with a limited amount of water to form a reaction mixture from which an appropriate chlorosiloxane is isolated. The chlorosiloxane is then treated with an alcohol to yield the alkoxysiloxane. Such routes, however, often yield mixtures from which it is difficult to separate the desired alkoxysiloxane.

Kenney et al. in U.S. Pat. No. 4,717,773 teach an alternative route to alkoxysilanes and oligomeric alkoxysiloxanes comprising reacting a metal silicate with a strong acid-alcohol solution and then esterifying the resultant product with an alcohol. The only acids taught in this work, however, are strong acids such as HCl.

The present inventors have now discovered that alkoxysilanes and oligomeric alkoxysiloxanes can be made by reacting metal silicates with an acid selected from the group consisting of sulfurous acid or acids with a pKa greater than about 2.5 and then esterifying the resultant product with an alcohol.

SUMMARY OF THE INVENTION

The present invention relates to a novel method of preparing alkoxysilanes. The method comprises reacting a metal orthosilicate with an acid selected from the group consisting of sulfurous acid and acids with a pKa greater than about 2.5 in the presence of an alcohol. The product is then esterified by reacting it with ROH to form $Si(OR)_4$ wherein R is an alkyl of 1-20 carbon atoms.

The present invention also relates to a novel method of preparing oligomeric alkoxysiloxanes. The method comprises reacting a metal silicate having a framework that is the same as that of the desired alkoxysiloxane or is similar to it with an acid selected from the group consisting of sulfurous acid and acids with a pKa greater than about 2.5 in the presence of an alcohol. The product is then esterified by reacting it with ROH to form the oligomeric alkoxysiloxane, wherein R is an alkyl of 1-20 carbon atoms.

DETAILED DESCRIPTION OF THE INVENTION

The present invention is based on the discovery that acids which are only weak or moderate in strength can be used for the conversion of silicates to alkoxysilanes or oligomeric alkoxysiloxanes. This reaction sequence can be summarized for alkoxysilanes as follows:

Metal Orthosilicate + acid $\xrightarrow{ROH}$ $Si(OH)_4$    I

$Si(OH)_4$ + ROH $\longrightarrow$ $Si(OR)_4$ + $H_2O$    II

The corresponding equations for oligomeric alkoxysiloxanes are:

Metal silicate + acid $\xrightarrow{ROH}$ Polysilicic Acid    III

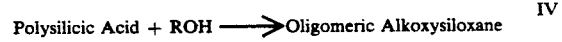

Polysilicic Acid + ROH $\longrightarrow$ Oligomeric Alkoxysiloxane    IV

It is to be noted that the silicic acid ($Si(OH)_4$) of equation I and the polysilicic acid of equation III are rarely obtained in a pure form. Rather, a mixture of silicon species is generally obtained. With the silicic acid of equation I, a mixture consisting of the partially reacted silicate, the silicic acid, the partially esterified silicic acid, and the esterified silicic acid is often obtained. With the polysilicic acid of equation III, a mixture consisting of the partially reacted silicate, the polysilicic acid, the partially esterified polysilicic acid, and the esterified polysilicic acid is often obtained. Similarly, a mixture of by-produced silicon species is also obtained with the alkoxysilanes of equation II and the alkoxysiloxanes of equation IV. It is to be further noted that the Si—O framework of the polysilicic acid may differ slightly from that of the silicate and that the framework of the alkoxysiloxane may differ slightly from that of the polysilicic acid.

The metal orthosilicates useful herein include any which can be converted to alkoxysilanes with the acids described herein. Such silicates can include, for example, sources of the orthosilicate ion ($SiO_4^{4-}$) such as beta-$Ca_2SiO_4$, gamma-$Ca_2SiO_4$, $CaMgSiO_4$, $Zn_2SiO_4$, or $Li_4SiO_4$ as well as other agents such as $Ca_3SiO_5$, portland cement ($Ca_3SiO_5$ and beta-$Ca_2SiO_4$), etc., which are all well known in the art and readily available.

The metal silicates useful in equation III include any which can be converted to the oligomeric alkoxysiloxanes with the acids described herein. Generally, these silicates provide the Si—O framework in whole or in part to the desired oligomer. Such silicates can include, for instance, sources of $Si_2O_7^{6-}$, $Si_3O_9^{6-}$, $Si_4O_{12}^{8-}$, and $Si_6O_{18}^{12-}$. Specific examples of compounds include $Ca_2ZnSi_2O_7$ (hardystonite), $Ca_8Si_4O_{12}Cl_8$, $Zn_4Si_2O_7 \cdot (OH)_2*H_2O$, $Ca_2MgSi_2O_7$, $Ca_3Si_3O_9$, etc., which are all well known in the art and readily available.

The acids described herein include sulfurous acid and acids with a pKa greater than about 2.5. Such acids are generally used in at least a stoichiometric amount, i.e., at least an amount which provides one available $H^+$ for each pendent oxygen of the silicate anion. In addition, the form and concentration of such acids are not critical and can vary over a wide range.

Though other acids may be used herein those preferred include sulfurous, acetic and carbonic. Since sulfurous acid is unstable and cannot be isolated in its pure form, it is generally produced by the reaction of water with sulfur dioxide in a water-alcohol solution. Use of this agent is seen to be very advantageous especially since $SO_2$ is a waste gas from the smelting of copper sulfide ores and from certain other industrial operations. Moreover, when this agent is reacted with $Ca_2SiO_4$, the following loop can be formed with water as the only by-product:

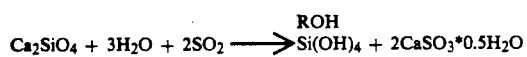

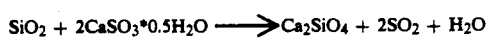

The acetic acid used in the above process can be generated by processes well known in the art such as the oxidation of acetaldehyde. This agent is commercially available in a variety of concentrations and can be used herein by merely adding it to the reactant mixture.

If carbonic acid is used it is generally produced by the reaction of water with carbon dioxide in a water-alcohol solution. This reaction is of particular interest since the reactants are inexpensive and easy to handle. Moreover, if this agent is reacted with $Ca_2SiO_4$, the following loop can be formed with water as the only by-product:

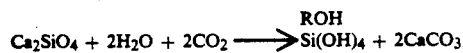

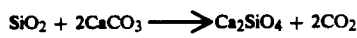

Since the acids used in the above process are only weak to moderate in strength, it was particularly unexpected that these acids together with alcohols could be used to make alkoxysilanes and alkoxysiloxanes. Because such acids do function herein however it is seen to be particularly advantageous since relatively mild reaction conditions may be used and since undesirable by-products (such as $CaCl_2$ when HCl is used) are not generated.

Reaction of the metal orthosilicate (I) or the metal silicate (III) is generally accomplished by merely adding the powdered silicate to a solution of the acid in an alcohol or by adding the acid to a suspension of the silicate in the alcohol. Facilitating measures such as stirring and heat may be used as necessary to increase the dissolution and reaction. Generally, stirring the mixture at a temperature of about $-30°$ C. up to about $100°$ C. is functional herein. Preferably, the mixture is stirred at about $0°$ C. to about $45°$ C.

Alcohol is included in the above reaction mixture to act as a solvent for the acid and reaction products as well as to stabilize the silicic acid or polysilicic acid as it is produced. The stabilization achieved is believed to occur by the alcohol hydrogen bonding to the silicic acid or polysilicic acid molecules, thereby forming protective sheaths around them. It should be noted that the alcohol chosen may have an effect on the protection afforded.

The alcohols which are functional herein include those of the formula ROH wherein R is an alkyl group of 1–20 carbon atoms. Representative examples, therefore, include methanol, ethanol, propanol butanol, etc. It is to be noted that the alcohol used in this reaction is generally the same as that used in esterification since some esterification may occur during this reaction. The amount of alcohol to be used herein is generally not critical, but enough should be used to produce a dilute solution of the silanol. Therefore, silicate-to-alcohol molar ratios of less than about $1 \times 10^{-2}$ are often employed.

After the silicic acid or polysilicic acid is obtained as in equations I and III it is then esterified by reaction with the alcohol. While this reaction apparently will occur in the weak to moderate acid medium, it will probably not occur at a rate which is practical for large-scale production. Therefore, in a preferred embodiment of this invention said reaction is often catalyzed by the addition of a catalytic amount of a strong acid, preferably HCl. It is noted that removal of by-products from the previous reaction can decrease the requisite amount of acid catalyst.

The above esterification in equations II and IV is merely accomplished by reacting the silicic acid or polysilicic acid with the alcohol, preferably in the presence of an agent which will azeotrope out the by-produced water, and an acid catalyst. Again, facilitating measures such as stirring and heat may be used to increase this reaction. Generally, this reaction is conducted at $50°$ C. to about $150°$ C. with temperatures in the range of about $75°$ C. to $100°$ C. being preferred.

The azeotroping agent is preferably used in this stage of the reaction so that water is distilled out as it is formed. This thereby drives the reaction forward. Azeotroping agents useful herein are well known in the art and may include aromatic hydrocarbons such as benzene, toluene and xylene; chloroform; and various alcohols. It is to be noted that if azeotroping alcohols are used as solvents/esterifying agents, it may not be necessary to add further azeotroping agents for this reaction. The amount of azeotroping agent to be used herein is not critical, but it should generally be used in an amount sufficient to remove most of the by-produced water.

The alcohols useful in the esterification reaction are the same as those used to stabilize the silicic acid or polysilicic acid. Generally, such alcohols are incorporated herein in at least a stoichiometric amount, i.e., at least an amount which provides one ROH for each OH of the silicic acid or silicic acid derivative.

After the alkoxysilane or oligomeric alkoxysiloxane has been formed, it is merely removed from the solvent by any convenient and conventionally known means. Methods such as fractional vacuum distillation, extraction with an organic solvent and supercritical fractionation are useful and contemplated herein.

The isolated products can be either liquids or solids and they are useful as synthetic intermediates in the production of, for instance, polysiloxane resins.

The following non-limiting examples are provided so that one skilled in the art may more fully understand the invention.

EXAMPLE 1 Si(OC$_2$H$_5$)$_4$ FROM beta-Ca$_2$SiO$_4$ USING SULFUROUS ACID

A stream of SO$_2$ was passed through a degassed solution of 800 mL of ethanol and 15 mL of water for 15 hours. 9.66 g of beta-Ca$_2$SiO$_4$ was added to the solution and the suspension formed was stirred for 3.25 hours at about 57° C. The suspension was filtered and the solid was washed with 50 mL of pentane. The filtrate and washings were combined and added at 15 mL/min to a solution comprised of 1.0 mL of a 9.3 N solution of HCl in ethanol. 900 mL of ethanol and 1.00 L of toluene which was being distilled at 35 mL/min. Distillation was continued until 2.50 L of distillate was collected. The remaining suspension was filtered and the solid was washed with 30 mL of pentane. The filtrate and washings were combined and then concentrated by rotary evaporation (25° C./60 torr). The concentrate was vacuum distilled and an appropriate fraction (70°–75° C./30 torr) was retained. The fraction was identified by gas chromatography to be Si(OC$_2$H$_5$)$_4$ with a 14% yield.

EXAMPLE 2 (n—C$_3$H$_7$O)$_4$Si FROM BETA-Ca$_2$SiO$_4$ USING SULFUROUS ACID

A stream of SO$_2$ was passed through a degassed solution of 1.40 L of 1-propanol and 18 mL of water for 10 hours. 9.32 g of beta-Ca$_2$SiO$_4$ was added to the solution obtained and the suspension formed was stirred for 3 hours at about 43° C. The resultant suspension was filtered and the solid was washed with 15 mL of pentane. The filtrate and washings were combined and added at 30 mL/min to a solution comprised of 1.0 mL of an 8.5 N solution of HCl in 1 propanol and 2.00 L of 1-propanol which was being distilled at 35 mL/min. Distillation was continued until 2.62 L of distillate was collected. The remaining solution was concentrated by rotary evaporation (25° C./60 torr). The concentrate was vacuum distilled and an appropriate fraction (63°–68° C./1 torr) was retained. The fraction was identified by gas chromatography to be (n—C$_3$H$_7$O)$_4$Si with a 33% yield.

EXAMPLE 3 (n—C$_3$H$_7$O)$_4$Si FROM PORTLAND CEMENT USING SULFUROUS ACID

A stream of SO$_2$ was passed through a degassed solution of 800 mL of 1-propanol and 15 mL of water for 10 hours. 13.9 g of portland cement (Maryneal zero C3A Type III. Lone Star Industries. Houston, Texas) was added to the solution obtained and the suspension formed was stirred for 2.75 hours at about 57° C. The resultant suspension was filtered and the solid was washed with 200 mL of pentane. The filtrate and washings were combined and added at 20 mL/min to a solution comprised of 1.5 mL of a 4.5 N solution of HCl in 1-propanol and 1.30 L of 1-propanol which was being distilled at 20 mL/min. Distillation was continued until 1.65 L of distillate was collected. 400 mL of toluene was added to the remaining solution and the solution was again distilled until 450 mL of distillate was collected. The suspension remaining was filtered and the solid washed with 120 mL of pentane. The filtrate and washings were combined and then concentrated by rotary evaporation (25° C./60 torr). The concentrate was vacuum distilled and an appropriate fraction (66°–72° C./1 torr) was retained. The fraction was identified by gas chroxatography to be (n—C$_3$H$_7$O)$_4$Si with a 14% yield.

EXAMPLE 4 (n—C$_3$H$_7$O)$_3$SiOSi(O—n—C$_3$H$_7$)$_3$ FROM Ca$_2$ZnSi$_2$O$_7$ USING SULFUROUS ACID

A stream of SO$_2$ was passed through a degassed solution of 800 mL of 1-propanol and 15 mL of water for 13 hours. 9.50 g of Ca$_2$ZnSi$_2$O$_7$ was added to the solution obtained and the suspension formed was stirred for 20 minutes at about 47° C. The resultant suspension was filtered and the solid was washed with 20 mL of pentane. The filtrate and washings were combined and added at 20 mL/min to a solution comprised of 1.5 mL of a 4.5 N solution of HCl in 1-propanol and 1.20 L of 1-propanol which was being distilled at 30 mL/min. Distillation was continued until 1.65 L of distillate was collected. 420 mL of toluene was added to the remaining solution and the solution was again distilled until 500 mL distillate was collected. The suspension remaining was filtered and the solid washed with 100 mL of pentane. The filtrate and washings were combined and then concentrated by rotary evaporation (25° C./60 torr). The concentrate was vacuum distilled and an appropriate fraction (125°–132° C./10 torr) was retained. The fraction was identified by gas chromatography to be (n—C$_3$H$_7$O)$_3$SiOSi(O—n—C$_3$H$_7$)$_3$ with an 11% yield.

EXAMPLE 5 [(n—C$_3$H$_7$O)$_2$SiO]$_4$ FROM Ca$_8$Si$_4$O$_{12}$Cl$_8$ USING SULFUROUS ACID

A stream of SO$_2$ was passed through a degassed solution of 800 mL of 1-propanol and 18 mL of water for 12 hours. 19.9 g of Ca$_8$Si$_4$O$_{12}$Cl$_8$ was added to the solution obtained and the suspension formed was stirred for 40 minutes at about 51° C. The resultant suspension was filtered and the solid was washed with 50 mL of pentane. The filtrate and washings were combined and added at 14 mL/min to a solution comprised of 2.1 mL of a 4.5 N solution of HCl in 1-propanol and 1.20 L of 1-propanol which was being distilled at 30 mL/min. Distillation was continued until 1.70 L of distillate was collected. 400 mL of toluene was added to the remaining solution and the solution was again distilled until 420 mL of distillate was collected. The suspension remaining was filtered and the solid washed with 200 mL of pentane. The filtrate and washings were combined and then concentrated by rotary evaporation (25° C./60 torr). The concentrate was vacuum distilled and an appropriate fraction (165°–173° C./10 torr) was retained. The fraction was identified by gas chromatography to be [(n—C$_3$H$_7$O)$_2$SiO]$_4$ with a 19% yield.

EXAMPLE 6 (n—C$_3$H$_7$O)$_4$Si FROM BETA-Ca$_2$SiO$_4$ USING ACETIC ACID

A slurry of 7.76 g of beta-Ca$_2$SiO$_4$, 800 mL of 1-propanol and 20.0 mL of 99.7% acetic acid was stirred for 2.5 hours at about 40° C. The resultant suspension was filtered and the solid was washed with 50 mL of 1-propanol. The filtrate and washings were combined and added at 20 mL/min to a solution comprised of 0.90 mL of an 8.5 N solution HCl in 1-propanol and 1.00 L of 1-propanol which was being distilled at 20 mL/min. Distillation was continued until 1.69 L of distillate was collected. 300 mL of toluene was added to the remaining solution and the solution was again distilled until 300 mL of distillate was collected. The suspension remaining was filtered and the solid was washed with 50 mL of pentane. The filtrate and washings were combined and then concentrated by rotary evaporation (25° C./60 torr). The concentrate was vacuum distilled and an appropriate fraction (71°-75° C./1 torr) was retained. The fraction was identified by gas chromatography to be $(n-C_3H_7O)_4Si$ with a 10% yield.

EXAMPLE 7 $(n-C_3H_7O)_4Si$ FROM PORTLAND CEMENT USING ACETIC ACID

A slurry of 534 mg of portland cement (Maryneal zero C3A Type III, Lone Star Industries, Houston, Texas), 100 mL of 1-propanol and 0.80 mL of 99.7% acetic acid was stirred for 3.25 hours at about 45° C. The resultant suspension was filtered and the solid was washed with 10 mL of 1-propanol. The filtrate and washings were combined and added at 10 mL/min to a solution comprised of 0.10 mL of a 5.9 N solution of HCl in 1-propanol and 125 mL of 1-propanol which was being distilled at 8 mL/min. Distillation was continued until 165 mL of distillate was collected. The remaining solution contained $(n-C_3H_7O)_4Si$ with a 20% yield (identified by gas chromatography).

EXAMPLE 8 $Si(OC_2H_5)_4$ FROM BETA-$Ca_2SiO_4$ USING CARBONIC ACID

A mixture of 108 mg of beta-$Ca_2SiO_4$, 50 mL of ethanol and 18 mL of water was placed in a Parr Bomb. The Parr Bomb was sealed and 118 g of $CO_2$ was added to the mixture through an inlet valve. The resulting suspension was stirred for 30 minutes at about 40° C. and then the unreacted $CO_2$ was vented. The resultant suspension was filtered and the solid was washed with 50 mL of ethanol. The filtrate and washings were combined and added at 10 mL/min to a solution comprised of 50 microL of an 8.6 N solution of HCl in ethanol. 150 mL of ethanol and 200 mL of toluene which was being distilled at 15 mL/min. Distillation was continued until 310 mL of distillate was collected. The remaining solution contained $Si(OC_2H_5)_4$ with a 3% yield (identified by gas chromatography).

EXAMPLE 9 $Ca_2SiO_4$ AND $Ca_3SiO_5$ FROM $CaSO_3*0.5H_2O$ AND $SiO_2$

A mixture of 6.04 g of $CaSO_3*0.5H_2O$ and 1.31 g of amorphous $SiO_2$ powder was placed in a Pt dish and the dish was then put in an $N_2$-atmosphere furnace. Under a 20 mL/min flow of $N_2$, the mixture was heated at 100° C./hr to 860° C. and held at this temperature for 27 hours. The resulting solid was cooled at 100° C./hr to room temperature and was then crushed in air with a mortar and pestle to provide 6.35 g of product. 1.81 g of the powder was heated in a Pt crucible in air at 1475° C. for 2 hours. The resulting solid was cooled quickly in air and was crushed with a mortar and pestle to provide 1.21 g of product.

X-ray powder diffractometry of the above materials revealed about 55% gamma-$Ca_2SiO_4$, about 35% $Ca_3SiO_5$, about 5% CaO and about 5% CaS.

That which is claimed is:

1. A method of manufacturing alkoxysilanes comprising:
   a) reacting a metal orthosilicate with an acid selected from the group consisting of sulfurous acid and acids with a pKa greater than about 2.5 in the presence of an alcohol and then
   b) reacting the product of (a) with ROH to form $Si(OR)_4$, wherein R is an alkyl group of 1-20 carbon atoms.

2. The method of claim 1 wherein the acid is selected from the group consisting of sulfurous acid. acetic acid and carbonic acid.

3. The method of claim 1 wherein the reaction (b) is catalyzed by the addition of an acid.

4. The method of claim 3 wherein the acid catalyst is HCl.

5. The method of claim 1 wherein the metal orthosilicate is selected from the group consisting of beta-$Ca_2SiO_4$, $Ca_3SiO_5$, $Li_4SiO_4$, and portland cement.

6. The method of claim 1 wherein the alcohol of reaction (a) and ROH are the same and are selected from the group consisting of methanol, ethanol and propanol.

7. The method of claim 1 wherein the reaction (b) is run in the presence of an azeotroping agent.

8. The method of claim 8 wherein the azeotroping agent is selected from the group consisting of aromatic hydrocarbons and alcohols with 1-20 carbon atoms.

9. A method of manufacturing oligomeric alkoxysiloxanes comprising:
   a) reacting a metal silicate having a framework that is the same as or similar to that of the desired alkoxysiloxane with an acid selected from the group consisting of sulfurous acid and acids having a pKa greater than about 2.5 in the presence of an alcohol and then
   b) reacting the product of (a) with ROH to form the oligomeric alkoxysiloxane, wherein R is an alkyl group of 1-20 carbon atoms.

10. The method of claim 9 wherein the acid is selected from the group consisting of sulfurous acid. acetic acid and carbonic acid.

11. The method of claim 9 wherein reaction (b) is catalyzed by the addition of an acid.

12. The method of claim 11 wherein the acid catalyst is HCl.

13. The method of claim 9 wherein the metal silicate is selected from the group consisting of $Ca_2ZnSi_2O_7$ and $Ca_8Si_4O_{12}Cl_8$.

14. The method of claim 9 wherein the alcohol of reaction a) and ROH are the same and are selected from the group consisting of methanol, ethanol, propanol and butanol.

15. The method of claim 9 wherein reaction (b) is run in the presence of an azeotroping agent.

16. The method of claim 15 wherein the azeotroping agent is selected from the group consisting of aromatic hydrocarbons and alcohols with 1-20 carbon atoms.

17. A method of manufacturing alkoxysilanes without generating waste comprising:
   a) reacting water with sulfur dioxide to form sulfurous acid;
   b) reacting a metal orthosilicate with the sulfurous acid generated in step (a) in the presence of an alcohol to form a silicon species and a sulfite salt;
   c) separating the silicon species formed in step (b) from the sulfite salt;
   d) reacting the sulfite salt of step (c) with silicon dioxide to form the metal orthosilicate which can be reused in step (b) and sulfur dioxide which can be reused in step (a): and
   e) reacting the silicon species of step (c) with ROH to form $Si(OR)_4$, wherein R is an alkyl group of 1-20 carbon atoms.

18. The method of claim 17 wherein the metal orthosilicate is beta-$Ca_2SiO_4$.

19. The method of claim 17 wherein reaction (e) is catalyzed by the addition of an acid.

20. The method of claim 19 wherein the acid catalyst is HCl.

21. The method of claim 17 wherein the alcohol of reaction b) and ROH are the same and are selected from the group consisting of methanol, ethanol, propanol and butanol.

22. The method of claim 17 wherein reaction (e) is run in the presence of an azeotroping agent.

23. The method of claim 22 wherein the azeotroping agent is selected from the group consisting of aromatic hydrocarbons and alcohols with 1-20 carbon atoms.

24. A method of manufacturing alkoxysilanes without generating waste comprising:
   a) reacting water with carbon dioxide to form carbonic acid:
   b) reacting a metal orthosilicate with the carbonic acid generated in step (a) in the presence of an alcohol to form a silicon species and a carbonate salt;
   c) separating the silicon species formed in step (b) from the carbonate salt;
   d) reacting the carbonate salt of step (c) with silicon dioxide to form the metal orthosilicate which can be reused in step (b) and carbon dioxide which can be reused in step (a): and
   e) reacting the silicon species of step (c) with ROH to form $Si(OR)_4$, wherein R is an alkyl group of 1-20 carbon atoms.

25. The method of claim 24 wherein the metal orthosilicate is beta-$Ca_2SiO_4$.

26. The method of claim 24 wherein reaction (e) is catalyzed by the addition of an acid.

27. The method of claim 26 wherein the acid catalyst is HCl.

28. The method of claim 24 wherein the alcohol of reaction b) and ROH are the same and are selected from the group consisting of methanol, ethanol, propanol and butanol.

29. The method of claim 24 wherein reaction (e) is run in the presence of an azeotroping agent.

30. The method of claim 29 wherein the azeotroping agent is selected from the group consisting of aromatic hydrocarbons and alcohols with 1-20 carbon atoms.

* * * * *